United States Patent [19]

Saito

[11] Patent Number: 5,215,887

[45] Date of Patent: Jun. 1, 1993

[54] GLUCOSE SENSOR MEASUREMENT

[75] Inventor: Atsushi Saito, Tokyo, Japan

[73] Assignee: NEC Corporation, Tokyo, Japan

[21] Appl. No.: 801,657

[22] Filed: Dec. 2, 1991

[30] Foreign Application Priority Data

Nov. 30, 1990 [JP] Japan .................. 2-329681

[51] Int. Cl.$^5$ ............... G01N 27/46; A61B 5/00; C12N 11/04; C12N 11/08
[52] U.S. Cl. .................................. 435/14; 435/4; 435/25; 435/174; 435/182; 204/403; 204/412; 204/418; 204/817
[58] Field of Search ................ 435/14, 4, 25, 174, 435/182; 204/403, 412, 418, 817, 195

[56] References Cited

U.S. PATENT DOCUMENTS

| 4,431,004 | 2/1984 | Bessman et al. | 204/403 |
| 4,703,756 | 11/1987 | Gough et al. | 204/403 |
| 4,894,339 | 1/1990 | Hanazato et al. | 435/182 |
| 4,935,105 | 6/1990 | Churchouse | 435/4 |

OTHER PUBLICATIONS

Casa et al., "pH-Based Enzyme Potentiometric Sensors"; Analytical Chemistry, vol. 57, pp. 1917–1925, 1985.

*Primary Examiner*—Michael G. Wityshyn
*Assistant Examiner*—Louise N. Leary
*Attorney, Agent, or Firm*—Leydig, Voit & Mayer

[57] ABSTRACT

Disclosed is a method of measuring glucose concentration of a sample solution using a glucose sensor having an ion-sensitive field-effect transistor which can detect pH change in the sample solution provided with a glucose oxidase-immobilized film formed on the ion-sensing section thereof, which comprise a step of measuring the output of the glucose sensor under a low level of dissolved oxygen in the enzyme-immobilized film; a step of measuring the output of the glucose sensor under a high level of dissolved oxygen in the enzyme-immobilized film; and a step of determining the glucose concentration of the sample solution from the difference between said two output values. The measuring system can be simplified and working efficiency can be improved since the present measuring method requires neither a buffer nor correct measuring of the sample solution or buffer.

4 Claims, 3 Drawing Sheets

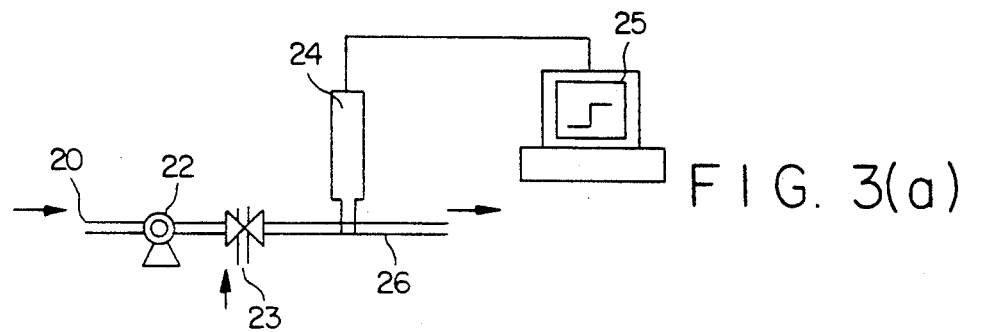
F I G. 3(a)
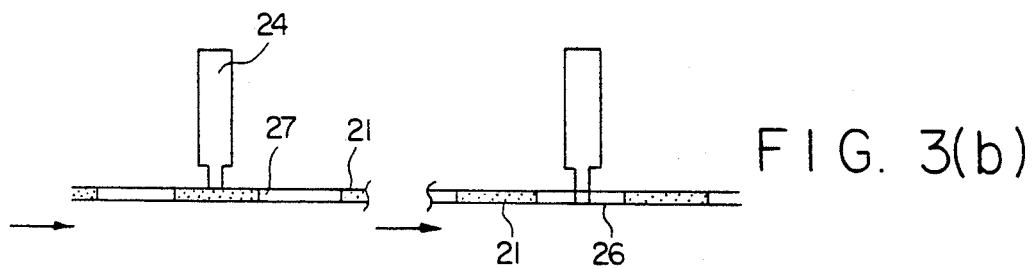
F I G. 3(b)
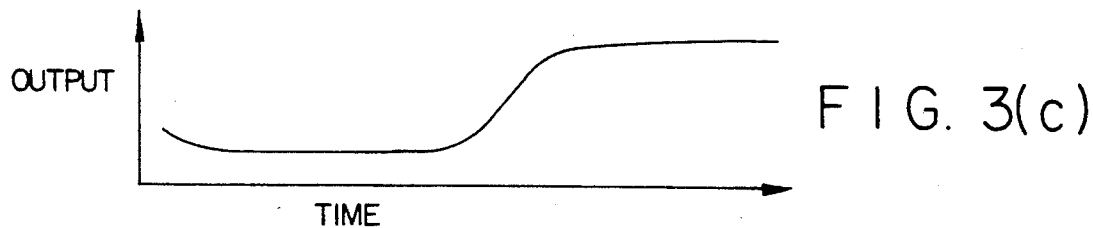
F I G. 3(c)

GLUCOSE SENSOR MEASUREMENT

BACKGROUND OF THE INVENTION

This invention relates to a method of measuring glucose concentration using a glucose sensor.

Various types of glucose sensors having a glucose oxidase-immobilized film provided on the ion-sensing section of an ion-sensitive field-effect transistor which detects pH change in sample solutions have so far been reported (Biophysica Biochimica Acta, Vol. 320, pp. 529-534, 1973; and Analytical Chemistry, Vol. 57, pp. 1917-1925, 1985). The principle of these sensors is to measure glucose level based on the pH change to be brought about by the catalytic action of glucose oxidase which oxidizes glucose to form gluconic acid. The reaction scheme that gluconic acid is formed from glucose is as follows:

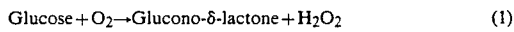

(1)

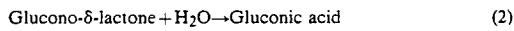

(2)

The reaction (1) takes place catalyzed by glucose oxidase. The reaction (2) proceeds spontaneously or catalyzed by gluconolactonase.

In the measurement of glucose using a glucose sensor of the type described above, the sensor is first dipped in a predetermined amount of buffer containing no glucose to measure a background output, and then a predetermined amount of sample solution is added to the buffer to measure a response output. The difference between the background output and the response output corresponds to the glucose concentration. This can be explained below referring to the attached drawings.

FIG. 1, (a) shows schematically a constitution of a system used for the glucose measurement by a conventional glucose sensor; FIG. 1(b) explains the measuring method using the same. FIG. 1(c) shows an output curve of the sensor corresponding to FIG. 1(b). The glucose sensor 33 is first dipped in a predetermined amount of buffer 31 to measure a sensor output. This output value is the background output. Next, a predetermined amount of sample solution 34 is added to the buffer 31 using a pipette 35, whereupon the output level of the sensor 33 increases. This is the response output. The output of the sensor in a series of process changes is shown in FIG. 1(c). Glucose concentration of the sample solution can be determined from the difference between the response output and the background output.

As described above, in the conventional glucose measuring method a buffer is inevitable and yet the buffer and sample solution must be measured correctly. Accordingly, in order to establish a system using a glucose sensor, the system requires a buffer and a measuring device, leading to increase in the size of the system, disadvantageously.

SUMMARY OF THE INVENTION

It is an object of this invention to provide a measuring method using a glucose sensor having overcome the above problems and requiring no buffer or measuring device.

A first aspect of this invention is directed to a method of measuring glucose concentration of a sample solution using a glucose sensor having an ion-sensitive field-effect transistor which can detect pH change in the sample solution provided with a glucose oxidase-immobilized film formed on the ion-sensing section thereof, which comprises a step of measuring the output of the glucose sensor under a low level of dissolved oxygen in the enzyme-immobilized film; a step of measuring the output of the glucose sensor under a high level of dissolved oxygen in the enzyme-immobilized film; and a step of determining the glucose concentration of the sample solution from the difference between said two output values.

A second aspect of this invention is directed to a method of measuring glucose concentration of a sample solution using a glucose sensor having an ion-sensitive field-effect transistor which can detect pH change in the sample solution provided with a glucose oxidase-immobilized film formed on the ion-sensing section thereof, which comprises a step of measuring the output of the glucose sensor under a low level of dissolved oxygen in the enzyme-immobilized film by exposing the sample solution to a gaseous atmosphere having an oxygen content lower than in air; a step of measuring the output of the glucose sensor under a high level of dissolved oxygen in the enzyme-immobilized film by exposing the sample solution to air; and a step of determining the glucose concentration of the sample solution from the difference between said two output values.

A third aspect of this invention is directed to a method of measuring glucose concentration of a sample solution using a glucose sensor having an ion-sensitive field-effect transistor which can detect pH change in the sample solution provided with a glucose oxidase-immobilized film formed on the ion-sensing section thereof, which comprises a step of measuring the output of the glucose sensor under a low level of dissolved oxygen in the enzyme-immobilized film by exposing the sample solution to air; a step of measuring the output of the glucose sensor under a high level of dissolved oxygen in the enzyme-immobilized film by exposing the sample solution to a gaseous atmosphere having an oxygen content higher than in air; and a step of determining the glucose concentration of the sample solution from the difference between said two output values.

A fourth aspect of this invention is directed to a method of measuring glucose concentration of a sample solution using a glucose sensor having an ion-sensitive field-effect transistor which can detect pH change in the sample solution provided with a glucose oxidase-immobilized film formed on the ion-sensing section thereof, which comprises a step of measuring the output of the glucose sensor by dipping the glucose sensor in the sample solution under a low level of dissolved oxygen in the enzyme-immobilized film; a step of measuring the output of the glucose sensor under a high level of dissolved oxygen in the enzyme-immobilized film by exposing the glucose sensor to a gaseous atmosphere containing oxygen; and a step of determining the glucose concentration of the sample solution from the difference between said two output values.

In this invention, a background output of the sensor is first measured under a low level of dissolved oxygen concentration in the enzyme-immobilized film (low level state). Since glucose oxidase requires oxygen when it oxidizes glucose, the output level of the sensor in this state is low. Next, a response output of the sensor is measured under a high level of dissolved oxygen concentration in the enzyme-immobilized film (high level state). When the dissolved oxygen concentration is at the high level, the sensor output is increased. The difference between the background output and the response output corresponds to the glucose concentration. Glucose level can be determined by providing such low level state and high level state by controlling the dissolved oxygen concentration, without using a buffer or diluting device.

p BRIEF DESCRIPTION OF THE DRAWINGS

FIG. 1(a) shows schematically the constitution of one embodiment of prior art measuring system;

FIG. 1(b) explains the measuring method using the embodiment of FIG. 1(a); and

Figure 1A:
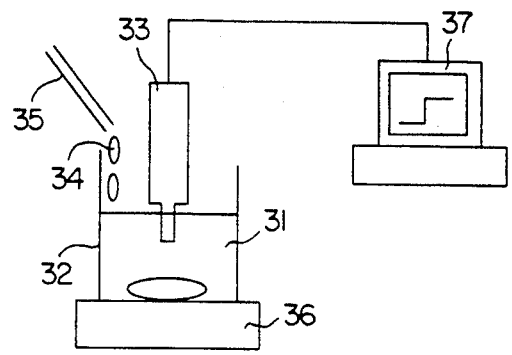
FIG. 1(c) shows an output curve of the sensor used in the embodiment of FIG. 1(a).
Figure 1B:
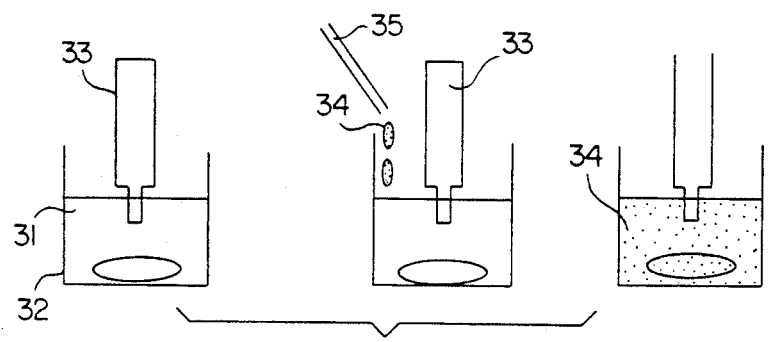
Figure 1C:
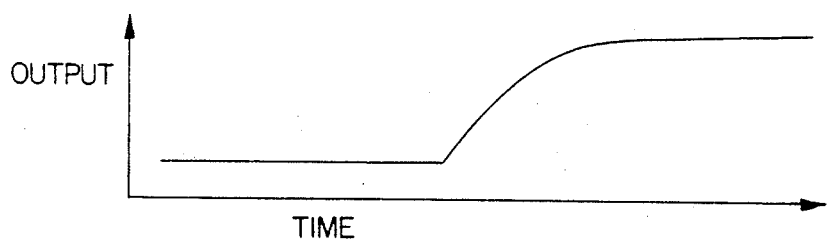
Figure 2A:
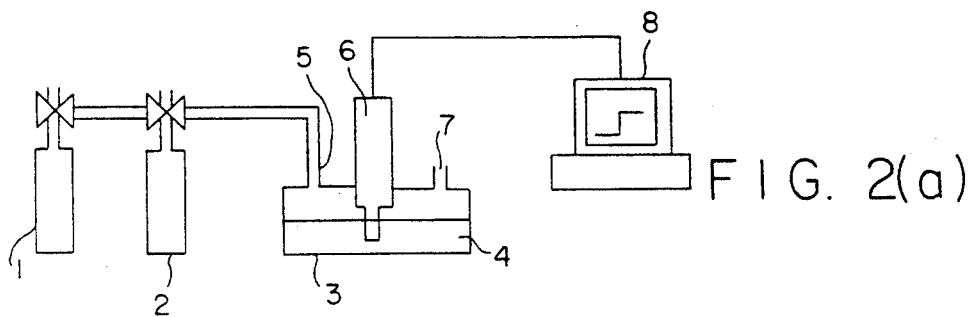
FIG. 2(a) shows schematically the constitution of one embodiment of the measuring system used according to the method of this invention.
Figure 2B:
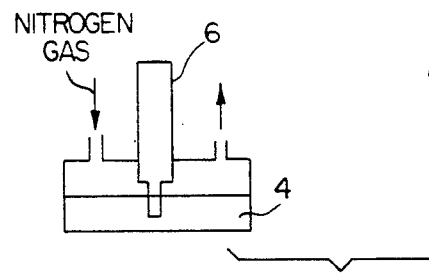
Figure 2B:
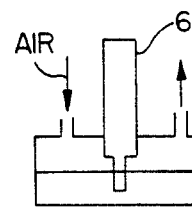
Figure 2C:
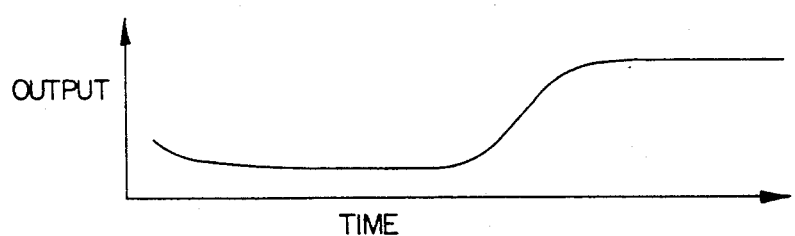

FIG. 2(b) explains the measuring method using the embodiment of FIG. 2(a);

FIG. 2(c) shows an output curve of the sensor used in the embodiment of FIG. 2(a);

FIG. 3(a) shows schematically the constitution of another embodiment of the measuring system used according to the method of this invention;

FIG. 3(b) explains the measuring method using the embodiment of FIG. 3(a);

FIG. 3(c) shows an output curve of the sensor used in the embodiment of FIG. 3(a);

DESCRIPTION OF THE PREFERRED EMBODIMENTS

Next, the preferred embodiments of this invention will be described specifically referring to the attached drawings.

FIG. 2(a) shows schematically the constitution of the measuring system used according to one embodiment of the inventive method. A glucose sensor 6 consists of an ion-sensitive field-effect transistor which detects pH change in a sample solution and has a glucose oxidase-immobilized film on the ion-sensing section thereof. The glucose oxidase-immobilized film is formed by adding the oxidase to a bovine serum albumin solution and crosslinking the mixture with glutaraldehyde. The gas inlet 5 communicates to the nitrogen gas tank 2 and to the air tank 1. While the output of the sensor 6 is not dependent on the amount of the sample solution, the measuring cell 3 has a capacity of 20 μl.

FIG. 2(b) explains the measuring method using the above system; and FIG. 2(c) shows an output curve corresponding to FIG. 2(b). A sample solution 4 is introduced to the measuring cell, and then, for example, nitrogen gas is introduced thereto from the nitrogen gas tank 2. After one minute, the measuring cell 3 is filled with nitrogen gas, so that the oxygen in the sample solution 4 and in the enzyme-immobilized film is purged. At this moment, the output of the sensor 6 is at a predetermined level, which is the background output. Next, air is introduced to the cell 3 from the air tank 1 instead of nitrogen gas. As the measuring cell 3 is filled with air, the oxygen concentrations in the sample solution 4 and in the enzyme-immobilized film are increased and saturated in about 3 minutes. Thus, the output level of the sensor 6 is increased, and the increased level is the response output. From the difference between the response output and the background output, the glucose concentration of the sample solution can be determined. According to such measuring method of this embodiment, neither a buffer nor correct measuring of the sample solution is necessary.

If the nitrogen gas is replaced with air and the air is replaced with a gas containing a high concentration of oxygen respectively in the above embodiment, an embodiment corresponding to the one as claimed in the appended claim 3 can be constituted. To describe in detail, a sample solution is introduced to the measuring cell, and air is introduced thereto. After one minute, the measuring cell is filled with air, and thus the oxygen concentrations in the sample solution and the enzyme-immobilized film show a predetermined level. At this moment, the sensor output is at a predetermined level, which is the background output. Next, a gas containing oxygen at a higher level than in air is introduced to the cell in place of air. As the measuring cell is filled with the gas, the oxygen concentrations in the sample solution and in the enzyme-immobilized film are increased and saturated in about 3 minutes. Thus, the output level of the sensor is increased, and the increased level is the response output. The glucose concentration of the sample solution can be determined from the difference between the response output and in the background output. According to such measuring method of this embodiment, neither a buffer nor correct measuring of the sample solution is necessary.

FIG. 3(a) shows schematically the constitution of another embodiment of the inventive measuring system. FIG. 3(b) explains the measuring method using the above system and FIG. 3(c) shows an output curve of the sensor corresponding to FIG. 3(b). The glucose sensor 24, like in FIG. 2, consists of of an ion-sensitive field-effect transistor which detects pH change in a sample solution and has a glucose oxidase-immobilized film on the ion-sensing section thereof. The glucose oxidase-immobilized film is formed by adding the oxidase to a bovine serum albumin solution and crosslinking the mixture with glutaraldehyde. The sample solution 21 is first introduced from the sample inlet 20 and fed to the gas/liquid feed pipe 26 via a liquid feeding pump 22 for 2 minutes. The concentration of the dissolved oxygen in the sample solution 21 is constant and at a low level, and so is the concentration of the dissolved oxygen in the enzyme-immobilized film. The output level of the sensor 24 is also at a predetermined level, and this is the background output. Next, when air 27 is introduced to the gas/liquid feed pipe 26 from the air inlet 23 for 2 minutes, the concentration of the dissolved oxygen in the enzyme-immobilized film is increased, and the increased level is the response output. From the difference between the response output and the background output, the glucose concentration of the sample solution can be determined. According to such measuring method of this embodiment, neither a buffer nor correct measuring of the sample solution is necessary.

As has been described heretofore, the measuring system can be simplified and working efficiency can be improved since the present measuring method requires neither a buffer nor correct measuring of the sample solution or buffer.

I claim:

1. A method of measuring glucose concentration of a sample solution using a glucose sensor having an ion-sensitive field-effect transistor which can detect pH change in the sample solution and is provided with a glucose oxidase-immobilized film formed on an ion-sensing section thereof, which comprises:

a step of measuring the output of the glucose sensor under a low level of dissolved oxygen in the glucose oxidase immobilized film;

a step of measuring the output of the glucose sensor under a high level of dissolved oxygen in the glucose oxidase immobilized film; and a step of determining the glucose concentration of the sample solution from the difference between the two measured outputs.

2. A method of measuring glucose concentration of a sample solution using a glucose sensor having an ion-sensitive field-effect transistor which can detect pH change in the sample solution and is provided with a glucose oxidase-immobilized film formed on an ion-sensing section thereof, which comprises;

a step of measuring the output of the glucose sensor under a low level of dissolved oxygen in the glucose oxidase immobilized film by exposing the sample solution to a gaseous atmosphere having an oxygen content lower than in air;

a step of measuring the output of the glucose sensor under a high level of dissolved oxygen in the glucose enzyme-immobilized film by exposing the sample solution to air; and a step of determining the glucose concentration of the sample solution from the difference between the two measured outputs.

3. A method of measuring glucose concentration of a sample solution using a glucose sensor having an ion-sensitive field-effect transistor which can detect pH change in the sample solution and is provided with a glucose oxidase-immobilized film formed on an ion-sensing section thereof, which comprises:

a step of measuring the output of the glucose sensor under a low level of dissolved oxygen in the glucose oxidase immobilized film by exposing the sample solution to air;

a step of measuring the output of the glucose sensor under a high level of dissolved oxygen in the glucose oxidase immobilized film by exposing the sample solution to a gaseous atmosphere having an oxygen content higher than in air; and a step of determining the glucose concentration of the sample solution from the difference between the two measured outputs.

4. A method of measuring glucose concentration of a sample solution using a glucose sensor having an ion-sensitive field-effect transistor which can detect pH change in the sample solution and is provided with a glucose oxidase-immobilized film formed on an ion-sensing section thereof, which comprises:

a step of measuring the output of the glucose sensor by dipping the glucose sensor in the sample solution under a low level of dissolved oxygen in the glucose oxidase immobilized film;

a step of measuring the output of the glucose under a high level of dissolved oxygen in the glucose oxidase immobilized film by exposing the glucose sensor to a gaseous atmosphere containing oxygen; and a step of determining the glucose concentration of the sample solution from the difference between the two measured outputs.

* * * * *

UNITED STATES PATENT AND TRADEMARK OFFICE
CERTIFICATE OF CORRECTION

PATENT NO. : 5,215,887
DATED : June 1, 1993
INVENTOR(S) : Atsushi Saito

It is certified that error appears in the above-indentified patent and that said Letters Patent is hereby corrected as shown below:

Claim 2, col. 5, line 24, change "enzyme-immobilized" to --oxidase immobilized--.

Claim 4, col. 6, line 25, after "glucose" insert --sensor--.

Signed and Sealed this

Eighteenth Day of January, 1994

Attest:

BRUCE LEHMAN

*Attesting Officer*   *Commissioner of Patents and Trademarks*